United States Patent [19]

Fukui

[11] Patent Number: 5,457,333
[45] Date of Patent: Oct. 10, 1995

[54] GAS SENSOR USED IN LEAK DETECTORS OR ALARM UNITS

[75] Inventor: Kiyoshi Fukui, Osaka, Japan

[73] Assignee: New Cosmos Electric Co., Ltd., Osaka, Japan

[21] Appl. No.: 155,548

[22] Filed: Nov. 22, 1993

Related U.S. Application Data

[63] Continuation of Ser. No. 749,653, Aug. 26, 1991, abandoned.

[30] Foreign Application Priority Data

Nov. 30, 1990 [JP] Japan .................... 2-340843

[51] Int. Cl.$^6$ ............... H01L 29/66; H01C 7/00; G01N 27/04; G08B 17/10
[52] U.S. Cl. ............ 257/253; 257/252; 257/414; 73/31.05; 73/31.06; 340/632; 340/634
[58] Field of Search ............... 73/31.06, 31.07, 73/31.05; 257/252, 253, 254, 414; 340/632, 633, 634

[56] References Cited

U.S. PATENT DOCUMENTS

| | | | |
|---|---|---|---|
| 4,030,340 | 6/1977 | Chang | 73/31.06 |
| 4,169,369 | 10/1979 | Chang | 73/23 |
| 4,198,850 | 4/1980 | Firth et al. | 73/31.06 |
| 4,358,951 | 11/1982 | Chang | 73/31.05 |
| 4,574,264 | 3/1986 | Takahashi et al. | 73/31.06 |
| 4,608,549 | 8/1986 | Fukui | 338/34 |
| 4,849,180 | 7/1989 | Fukui | 422/98 |
| 5,006,828 | 4/1991 | Yutaka et al. | 338/34 |
| 5,047,214 | 9/1991 | Fukui et al. | 422/98 |

FOREIGN PATENT DOCUMENTS

| | | | |
|---|---|---|---|
| 915458 | 11/1972 | Canada | 73/31.06 |
| 3922989A1 | 5/1990 | Germany . | |
| 56-112638 | 9/1981 | Japan | 73/31.06 |
| 112638 | 9/1981 | Japan | 73/31.06 |
| 46247 | 2/1987 | Japan | 73/31.06 |
| 47542 | 3/1987 | Japan | 73/31.06 |
| 63-109359 | 5/1988 | Japan | 73/31.05 |

OTHER PUBLICATIONS

Patent Abstract of Japan/Publication No. JP63109357/Combustion Safety Apparatus/Koda Hiroshi.
Patent Abstract of Japan/Publication No. JP62201344/Gas Sensor/Nakano Tomoyasu.

*Primary Examiner*—Sara W. Crane
*Assistant Examiner*—Alice W. Tang
*Attorney, Agent, or Firm*—Jones, Tullar & Cooper

[57] ABSTRACT

The invention relates to a gas sensor comprises a precious metal electrode, a semiconductor layer entirely or partly covering the precious metal electrode, a barrier layer having a high potential formed at an interface between the precious metal electrode and the semiconductor layer.

14 Claims, 8 Drawing Sheets

GAS SENSOR USED IN LEAK DETECTORS OR ALARM UNITS

This a continuation of application Ser. No. 07/749,653, filed on Aug. 26, 1991, abandoned

BACKGROUND OF THE INVENTION

1. Field of the Invention

This invention relates to gas sensors used in leak detectors or alarm units for detecting a fuel gas such as town gas or liquefied petroleum gas.

2. Description of the Related Art

Known semiconductor type gas sensors used in alarm units for detecting leakage of a fuel gas have sensitivity also to other gases than the fuel gas to be detected, such as hydrogen and alcohol gases. This is a major cause of false alarms. Thus, there are demands for semiconductor type gas sensors having reduced sensitivity to such interfering gases as hydrogen gas and alcohol gas, and excellent selectivity for a fuel gas or the like.

Figure 10:
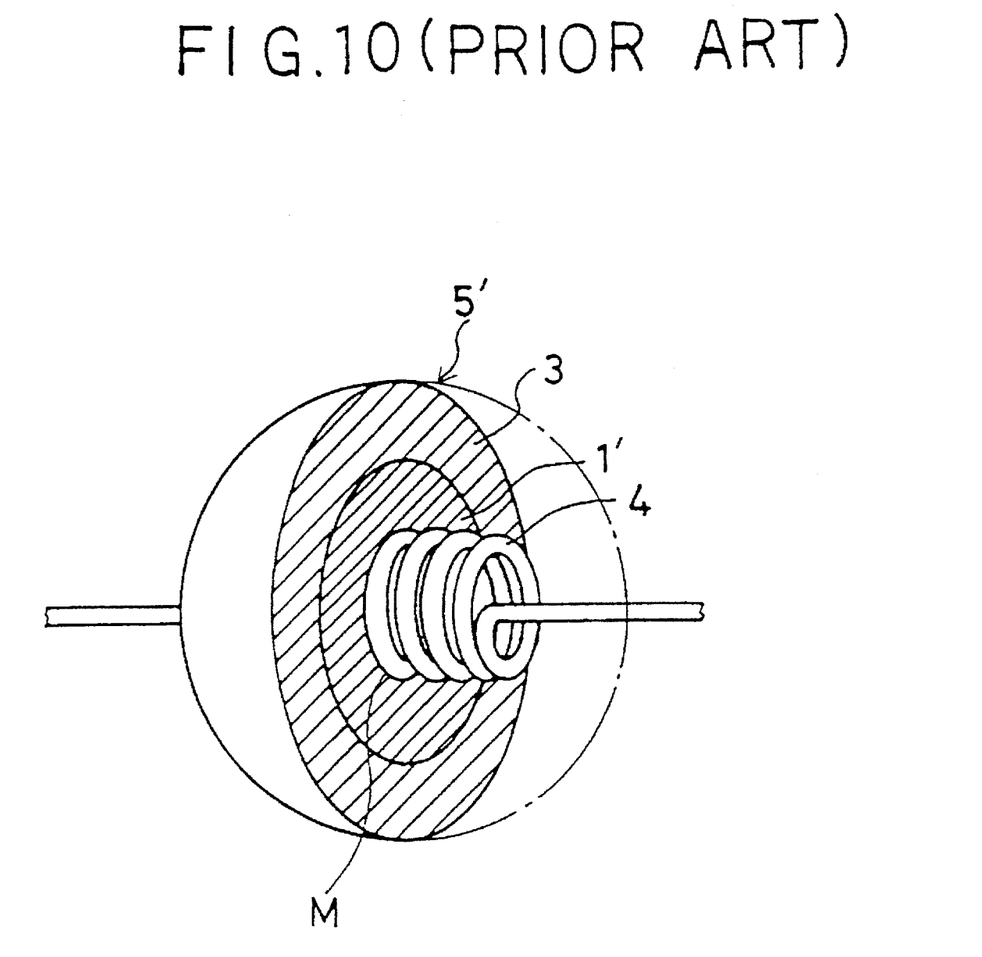
FIG. 10 is a perspective view, partly in section, of a known gas sensor.

In order to obtain a semiconductor type gas sensor having selective sensitivity to a particular gas, one of various active substances is included in a surface layer of the sensor to act as a filter layer or a filter layer of an active substance is additionally formed on the sensor. FIG. 10 shows an example of known semiconductor type gas sensors 5' having a filter layer 3. This sensor comprises a metal electrode 4 formed of platinum, which is covered by a metallic oxide semiconductor layer 1' of tin oxide ($SnO_2$), zinc oxide (ZnO) or the like. The metallic oxide semiconductor layer 1' is covered by a filter layer 3 including a support formed of alumina, for example, and supporting an active precious metal such as platinum or palladium.

With such a semiconductor type gas sensor 5', attention has been paid only to the metallic oxide semiconductor layer 1' or to its outer surface. In order to vary the sensor's sensitivity with regard to gas sensitivity, therefore, it has been conventional practice to mix an additive into the entire metallic oxide semiconductor layer 1' or apply it selectively to its outer surface. Alternatively, a plurality of such semiconductor layers formed on the sensor or a filter layer is added to the sensor.

Attempts have been made heretofore to improve the gas selectivity of the semiconductor type gas sensor with efforts made only in connection with the interface reaction between the gas atmosphere and metallic oxide semiconductor layer 1'. That is, although the semiconductor type gas sensor includes an interface M between the metallic oxide semiconductor layer 1' and the metal electrode 4, this interface M has been considered to have no direct relevance to gas sensitivity characteristics because the gas to be detected reacts within the semiconductor layer 1' before reaching the interface M.

The known semiconductor type gas sensor having a filter layer as noted above has the more complicated construction and requires the greater number of manufacturing steps for the filter layer, and therefore is not well suited for mass production. Further, such a semiconductor type gas sensor has a structural problem that combustion takes place at the filter layer upon contact with a high concentration fuel gas, whereby the semiconductor inside deteriorates through exposure to the resulting heat of reaction.

SUMMARY OF THE INVENTION

An object of the present invention is to provide a novel gas sensor which overcomes the disadvantages of the prior art and which has excellent selectivity for a fuel gas, without requiring a filter layer or the like, and therefore requires a simplified manufacturing process well suited for mass production.

The above object is fulfilled, according to the present invention, by a gas sensor comprising a precious metal electrode, and a semiconductor layer entirely or partly covering the precious metal electrode, wherein a barrier layer having a high potential is formed at an interface between the precious metal electrode and the semiconductor layer.

Intensive research has been conducted over the years with a view to realizing a semiconductor type gas sensor having a highly selective sensitivity to fuel gases with reduced sensitivity to interfering gases. It has been found as a result that the interface between a metallic oxide semiconductor layer and a metallic electrode, to which no attention has been paid heretofore, in fact plays an important role in gas sensitivity characteristics.

The surface of the metallic electrode has been regarded as an important part, and has formed the interface between the semiconductor layer and the metallic electrode, on the surface of which varied metals and semimetals (nonmetals) have been deposited to form surface potentials. Detailed experiments have been carried out to find out their influences on gas sensitivity characteristics. It has been found as a result that selectivity for a particular gas is obtained and the degree of selectivity is controllable, for example, by depositing on the electrode surface a metal of the same type as or a different type to the material forming the electrode. This is believed to closely relate to the state of a potential barrier formed at the interface between electrode and semiconductor layer (particularly the level of surface potential between electrode and semiconductor layer). It has been found that gas selectivity and sensitivity are variable particularly with variations in the surface activity due to various surface defects of the electrode. That is, a barrier layer having a high potential formed with the activity of the electrode surface suppressed, acts at a measuring time, to decrease detection sensitivity to miscellaneous gases such as hydrogen and alcohol.

Thus, according to a gas sensor embodying the present invention, a potential barrier higher than a Schottky barrier naturally produced by contact between a metal and a semiconductor is formed at the interface between a metallic electrode and semiconductor layer to determine a surface potential therebetween. This construction has the effect of suppressing the sensitivity to miscellaneous gases such as hydrogen and alcohol as opposed to various combustible gases, and providing selectivity for fuel gases.

The gas sensor of the present invention, therefore, does not require a filter layer or the like covering the semiconductor layer. This allows the sensor to have a very simple construction, and reduces the manufacturing process to be suited for mass production. Since the sensor does not include a filter layer, there occurs no combustion of a filter layer which would otherwise be caused by contact with a high concentration fuel gas. There is no chance of the semiconductor inside deteriorating through exposure to the strong heat of reaction, which would result in reduced sensitivity.

The gas sensor as constructed above has the sensitivity to detect various combustible gases, and the sensitivity to handle miscellaneous gases such as hydrogen and alcohol selectively reduced, whereby the sensitivity to fuel gases such as methane and propane is relatively improved. Further, it is possible to reduce the applied voltage dependence of the reduced sensitivity to miscellaneous gases.

Preferably, the barrier layer formed at the interface between the semiconductor layer and the precious metal electrode includes at least one substance selected from the group consisting of platinum, palladium, rhodium, gold, silver, copper and silicon oxide, and the semiconductor layer includes tin oxide as a main component.

With this construction, the gas sensor is capable of further suppressing the sensitivity to miscellaneous gases such as hydrogen and alcohol relative to various combustible gases and securing increased selectivity for fuel gases.

Other features and advantages of the present invention will be apparent from the following description.

DETAILED DESCRIPTION OF THE PREFERRED EMBODIMENTS

Gas sensors embodying the present invention will be described in detail with reference to the drawings.

Experimental examples will be described hereinafter, showing results obtained from the embodiments using tin oxide as a metallic oxide semiconductor layer which has a great influence on gas sensitivity characteristics.
(Experiment 1)

Figure 1:
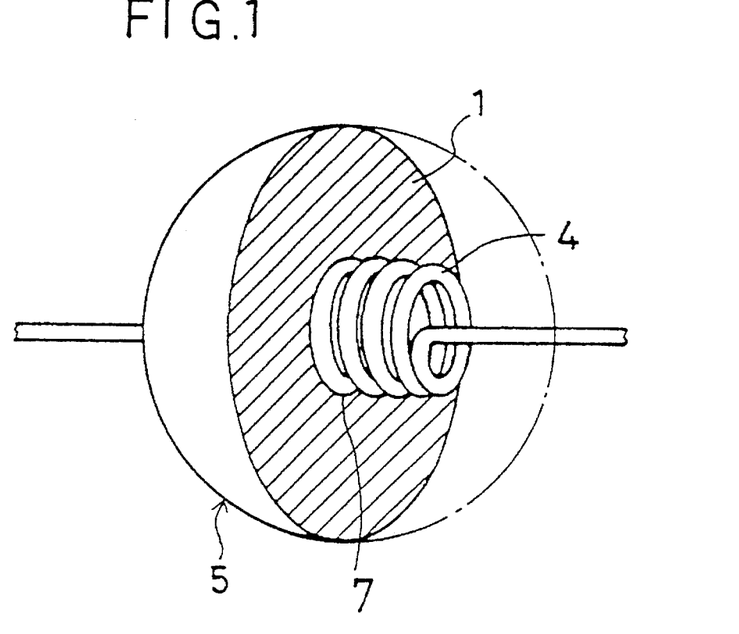
FIG. 1 is a perspective view, partly in section, of a gas sensor according to the present invention.

FIG. 1 shows a gas sensor in a first embodiment of this invention. This gas sensor 5 comprises a semiconductor layer 1 formed around a coiled electrode 4. The semiconductor layer 1 has a spherical shape about 0.45 mm in diameter, which has tin oxide as a main component to which antimony is added in 0.1 atomic %. The tin oxide having antimony added thereto is an oxide obtained by calcining in an electric furnace at about 600° C. a mixed gel of tin hydroxide and antimony hydroxide formed as a result of hydrolysis: dropping ammonia water to an aqueous solution of tin chloride and a small quantity of antimony chloride. The resulting tin oxide having antimony added thereto was dispersed in distilled water into paste form which was applied to the coiled electrode 4 to have the diameter of approximately 0.45 mm. Thereafter, a current is applied to the electrode 4 to effect sintering at about 600° C. to form the semiconductor layer 1.

The electrode 4 comprises a commercially available platinum wire (20 um$\phi$) wound several to tenodd times into a coil form. Next, platinum was deposited on the electrode 4 by applying a voltage of 2.0 V to an aqueous solution of 0.01 mol/l chloroplatinic acid, with the electrode 4 acting as a cathode and a platinum wire acting as an anode. This electrodeposition of platinum forms a platinum layer 7 on an outer surface of the electrode 4 to act as a barrier layer having a high surface potential. A plurality of gas sensors were manufactured by forming the semiconductor layer 1 on a plurality of electrodes 4 obtained by varying the electrodeposition time from 0 to 120 seconds.

Figure 2:
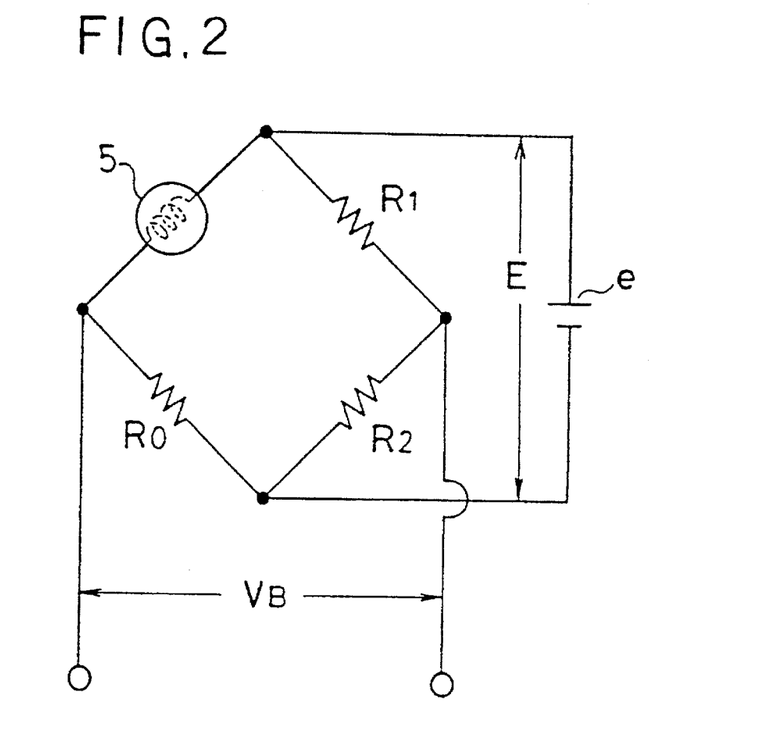
FIG. 2 is a view showing a principle of a bridge circuit for measuring output of the gas sensor.

These gas sensors were connected to a bridge circuit as shown in FIG. 2, to measure outputs of the sensor in clean air, in a gas of hydrogen in 1 vol %, and in a gas of methane in 1 vol %. This bridge circuit includes the gas sensor 5 and other fixed resistors R0, R1 and R2. A voltage E is applied from a power source e to the sensor to measure a bridge voltage VB as the sensor output. Relations among the above electrical factors are expressed by the equations set out below.

Output VB of the gas sensor 5 changes from Va to Vg when resistance Rsa of the gas sensor 5 in clean air changes to resistance Rsg thereof in an atmosphere of a reducing gas to be detected. The change $\Delta V$ in the sensor output VB is called sensitivity, which is defined by the following equation:

$$\Delta V \equiv Vg - Va \quad (1)$$

$\Delta V$ is derived from the following equation:

$$\Delta V = -E \frac{Rsg}{Rsg + R0'} - \frac{Rsa}{Rsa + R0'} \quad (2)$$

where E is a voltage applied to the sensor, and R0' is a resistance of the fixed resistor R0 which is a load resistor for the sensor.

Results obtained from this measurement circuit are set out below.

Figure 3:
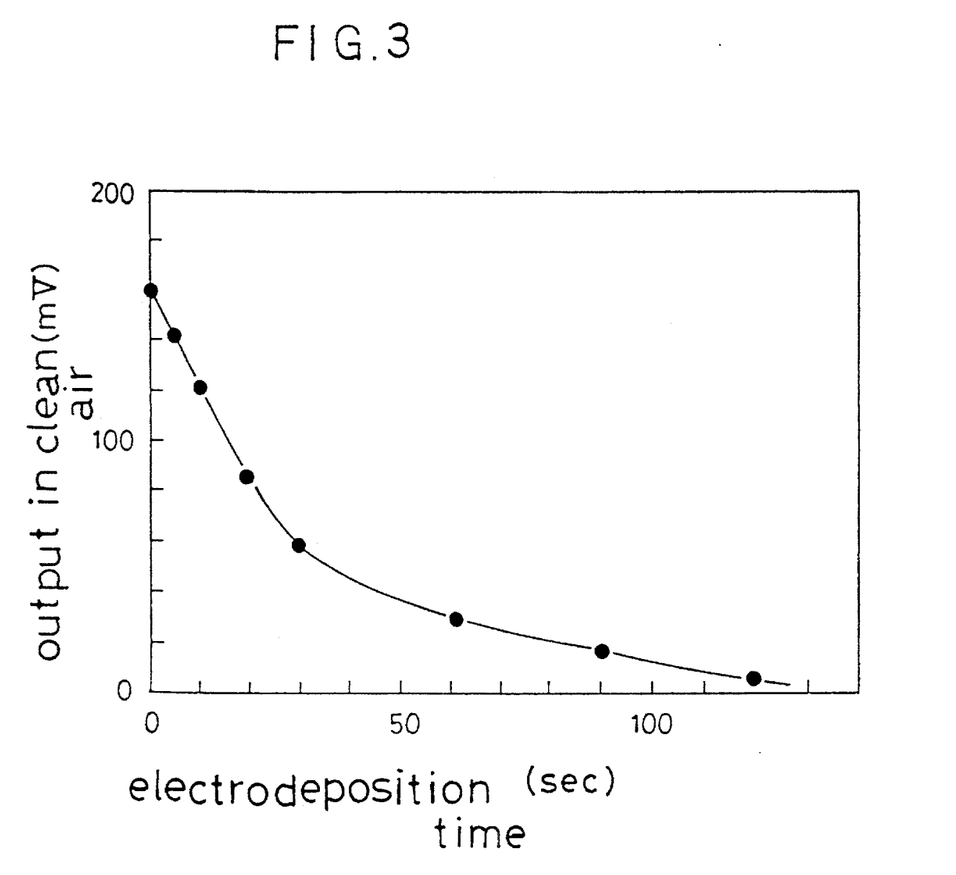
FIG. 3 is a graph showing electrodeposition time dependence of the output of the gas sensor in clean air.

FIG. 3 is a graph showing outputs of the various gas sensors in clean air in relation to electro-deposition time. This data are referred to hereinafter as data indicating electrodeposition time dependence. The data at zero electrodeposition time was obtained from a comparative example gas sensor having undergone no electrodeposition. The sensor output in clean air decreases with progress of electrodeposition time. In other words, the sensor resistance increases with progress of electrodeposition time. This increase is believed attributable to an increase in contact resistance between the platinum electrode and the tin oxide semiconductor, i.e. an increase in the potential barrier (an increase in the height thereof).

Figure 4:
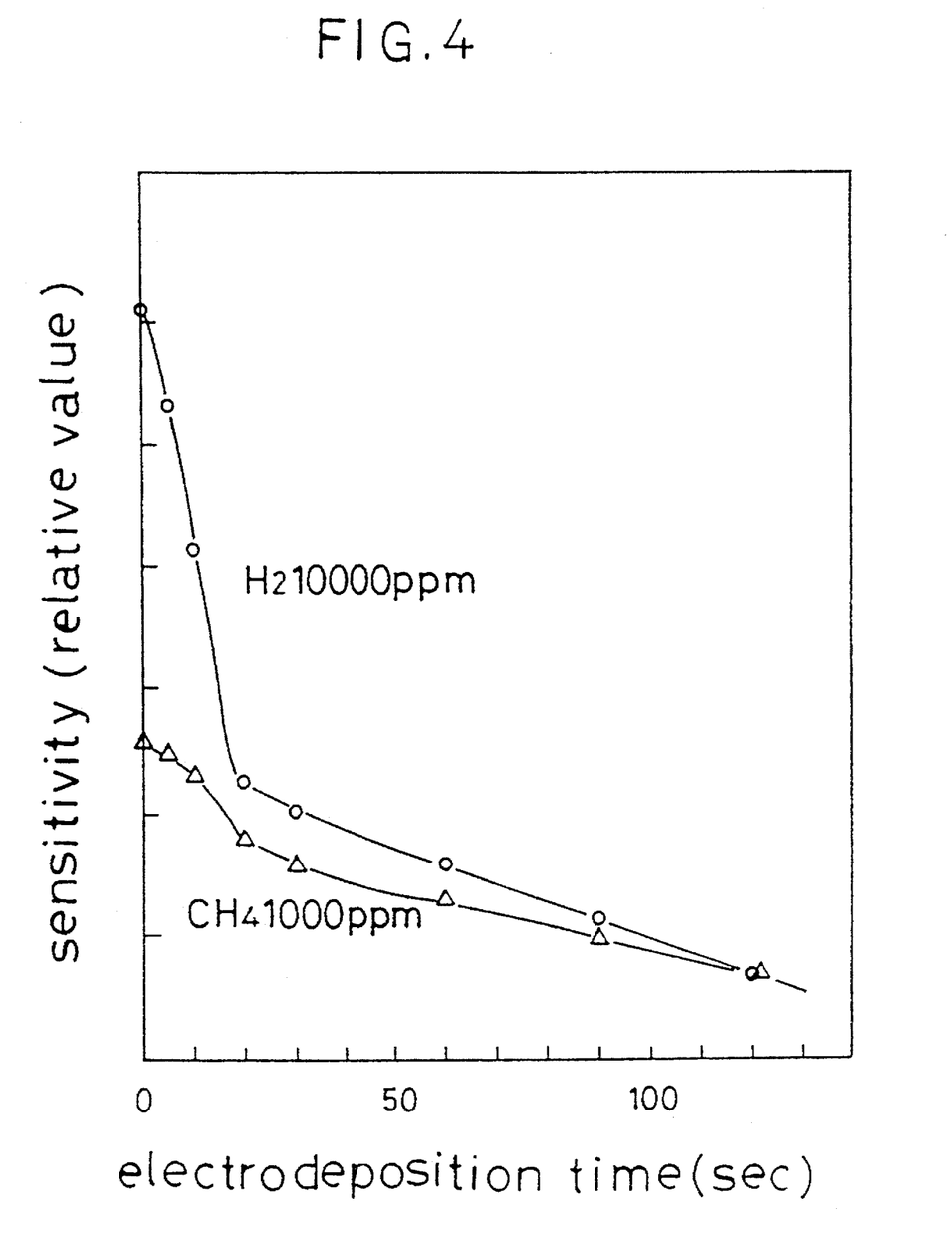
FIG. 4 is a graph showing electrodeposition time dependence of sensitivity to methane and hydrogen.
Figure 5:
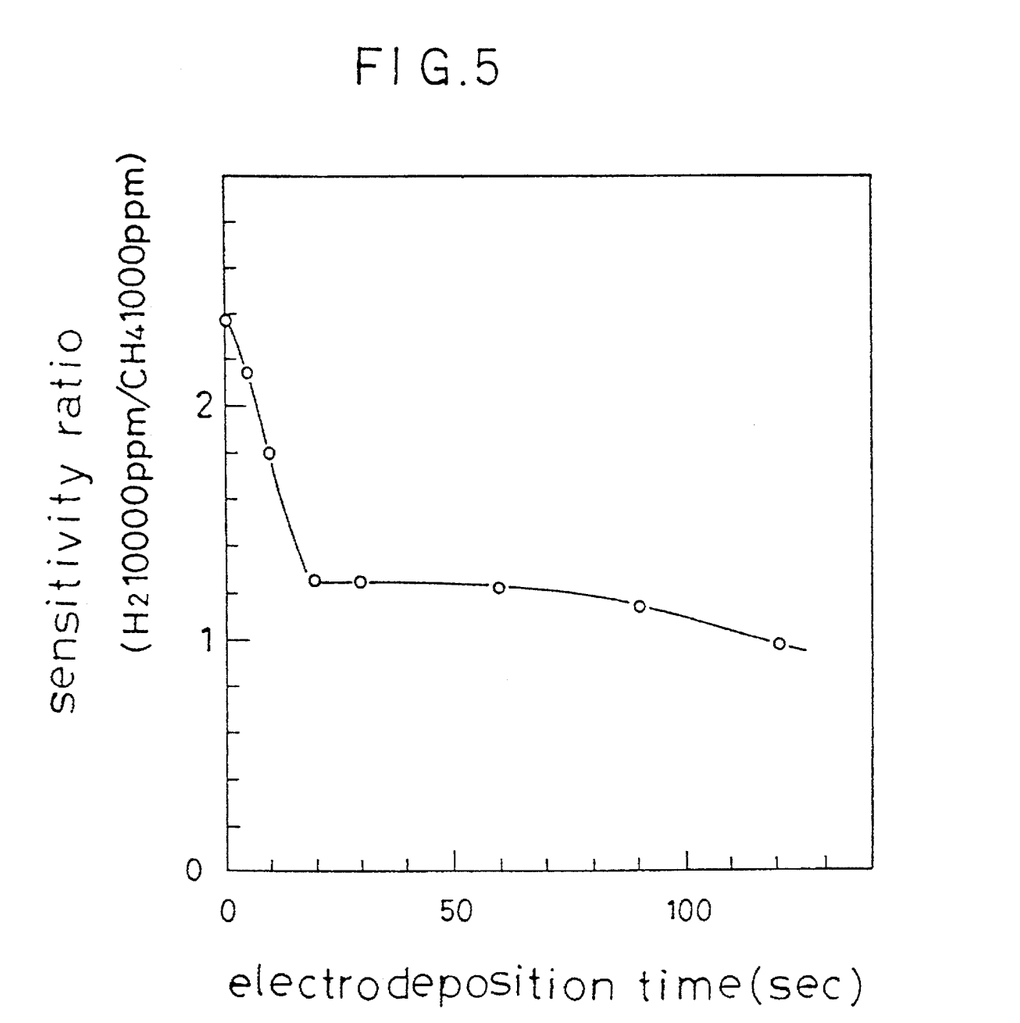
FIG. 5 is a graph showing electrodeposition time dependence of a hydrogen to methane sensitivity ratio, FIG. 6 (a) is a graph showing applied voltage dependence of sensitivity of a comparative example gas sensor A to various gases having a concentration of 1000 ppm.

FIG. 4 shows electrodeposition time dependence of sensitivity $\Delta V$ to methane (0.1 vol %) which is a typical example of fuel gases, and of sensitivity $\Delta V$ to hydrogen (1.0 vol %) which is a typical example of interfering gases. The sensitivity to hydrogen shows a sharp drop for the electrodeposition time up to 20 seconds (about a 64% decrease) and a gradual decline thereafter. Similarly, the sensitivity to methane decreases by 31% over the 20 second electrodeposition time, and gradually decreases thereafter. FIG. 5 shows electrodeposition time dependence of a hydrogen/methane sensitivity ratio (hydrogen: 1.0 vol %/methane: 0.1 vol %) resulting therefrom.

In FIG. 5, the sensitivity ratio decreases until a certain quantity of platinum is deposited in the 20 second electrodeposition time, and thereafter remains approximately constant. That is, the sensitivity ratio is improved by electrodepositing platinum in a certain quantity or more on the electrode.

The following are inferred from these phenomena:

(1) Sensitivity of the Gas Sensor

The relative sensitivity to a fuel gas to be detected is influenced by an increase, due to electrodeposition of platinum on the platinum electrode surface, of the potential barrier formed on the interface between the electrode and semiconductor layer described above, and by a chemical reaction of the gas occurring at the interface (mainly oxidation with adsorbed oxygen present on the tin oxide semiconductor surface and having a negative charge) and the resulting decrease of the potential barrier.

(2) Decrease in Relative Sensitivity of the Gas Sensor to Hydrogen

On the platinum electrode surface where platinum is electrodeposited, oxidation activity with respect to hydrogen much less than oxidation activity with respect to methane and isobutane in tile vicinity of operating temperature of the sensor. Consequently, it is believed that the reaction with methane decreases the potential barrier to a greater extent than the reaction with hydrogen, whereby the sensor has a greater selectivity for methane than for hydrogen.

Table 1 show quantities of platinum deposited on the platinum electrode surface which are derived from Faraday's law in the foregoing experiment.

It has been found, based on the result shown in Table 1, that platinum must be deposited in $1.3 \times 10^{-6}$ mol/cm$^2$ or more on the platinum electrode.

TABLE 1

| Quantities of Platinum Deposition (Calculated Values) | | |
|---|---|---|
| electrodeposition time t[sec] | platinum quantities | |
| | mol/cm$^2$ | mg/cm$^2$ |
| 20 | $1.3 \times 10^{-6}$ | 0.26 |
| 30 | $2.1 \times 10^{-6}$ | 0.40 |
| 60 | $4.2 \times 10^{-6}$ | 0.80 |
| 90 | $6.3 \times 10^{-6}$ | 1.2 |
| 120 | $8.4 \times 10^{-6}$ | 1.6 |

Conditions
electrolytic current: 1mA
electrode surface area: $3.8 \times 10^{-2}$ cm$^2$ FIGS. 6(a) and 6(b) show applied voltage dependence of sensitivity ΔV of a comparative example gas sensor A having no electrodeposit on the platinum electrode and a gas sensor B having platinum electrodeposited on the platinum electrode (electrodeposition time: 90 seconds) according to the present invention, respectively, to various gases in a concentration of 1000 ppm such as methane (CH$^4$), isobutane (i-C$_4$H$_{10}$), hydrogen (H$_2$), carbon monoxide (CO) and alcohol (C$_2$H$_5$OH).

Figure 6A:
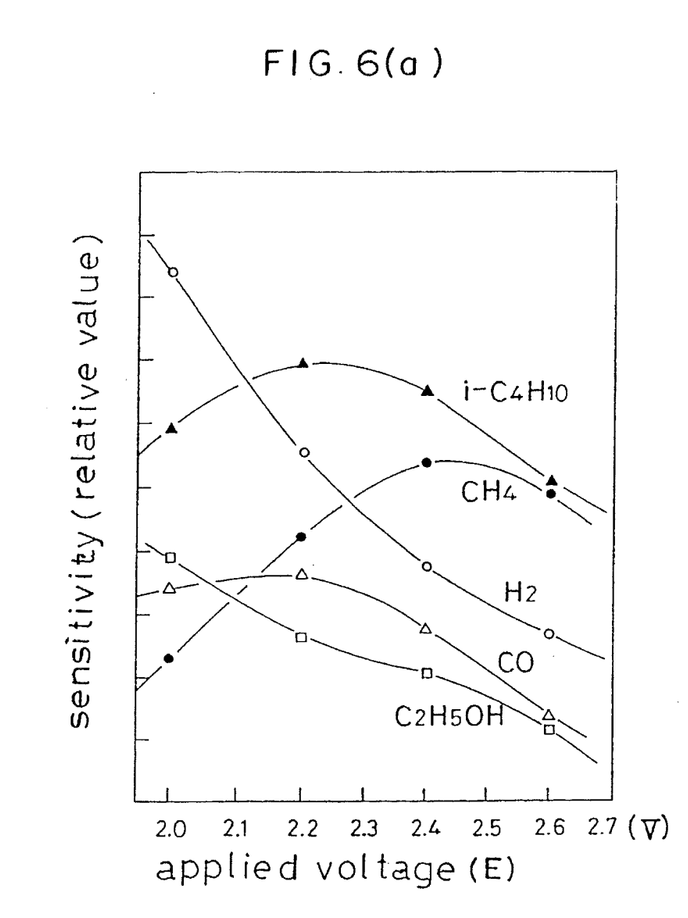
Figure 6B:
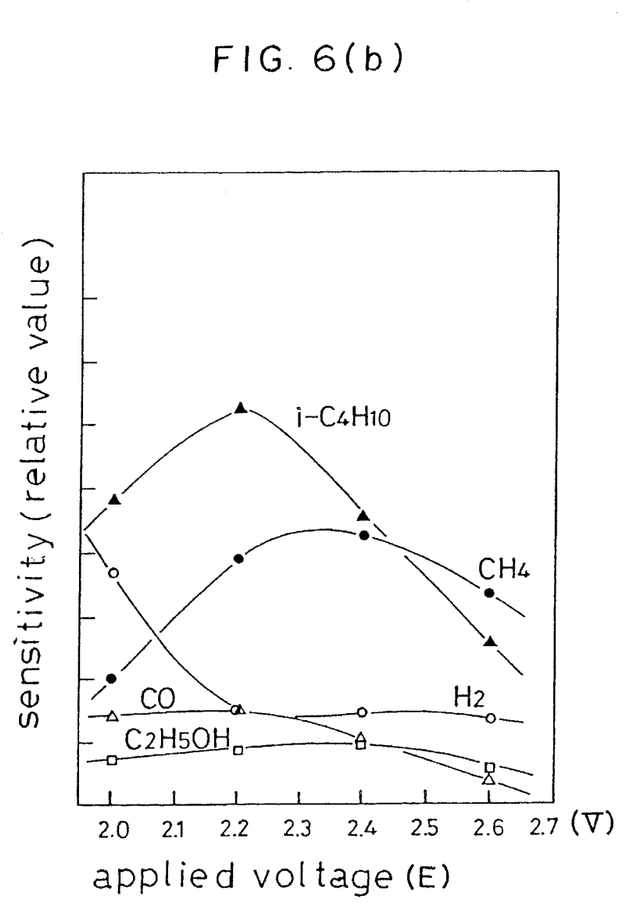
FIG. 6(b) is a graph showing applied voltage dependence of a gas sensor B of the present invention to various gases having a concentration of 1000 ppm.

It is seen from FIG. 6(b) that the gas sensor B of the present invention, with the same voltage applied to the sensor (about 2.3 V), has relative sensitivity to fuel gases such as isobutane and methane three to four times relative sensitivity to miscellaneous gases such as hydrogen, carbon monoxide and alcohol. On the other hand, as shown in FIG. 6 (a), the comparative example gas sensor A, with 2.3 V applied to the sensor, has relative sensitivity to fuel gases (particularly methane) only about the same as relative sensitivity to miscellaneous gases (particularly hydrogen). Thus, the gas sensor B of the present invention may be given excellent fuel gas selectivity with the relative sensitivity to miscellaneous gases reduced by appropriately choosing the voltage applied to the sensor.

Town gas alarm units mass-produced for household use, for example, are driven by simple source circuits having an error range of about ±1% in the voltage applied to the sensor to meet requirements for low cost and the like. Such a voltage application error presents no problem since alarm setting is effected for each household town gas alarm unit by using an actual gas to be detected such as isobutane and methane. With the household alarm unit, however, it is undesirable that the sensitivity to miscellaneous gases varies from unit to unit because of the error in voltage application to the sensor. Thus, the sensor is required to have reduced applied voltage dependence of the sensitivity to miscellaneous gases.

The electrodeposition time dependence of the sensitivity to miscellaneous gases shown in FIG. 6(b) is less than that in the comparative example shown in FIG. 6(a). In this sense too, the gas sensor B of the present invention is suited for town gas alarm units for household use.

(Experiment 2)

In Experiment 1 above, platinum was electrodeposited on the platinum electrode to vary activity on the platinum electrode surface, and the sensitivity of gas sensors to various gases was measured.

In Experiment 2, gas sensors were manufactured by electrodepositing other metals than platinum on the platinum electrode or forming a layer of silicon dioxide by chemical vapor deposition on the electrode, and the sensitivity of these sensors to fuel gases was compared with the sensitivity thereof to miscellaneous gases. These gas sensors have a similar construction to the gas sensors in Experiment 1 (see FIG. 1).

It often is the case with gas leak alarm units for industrial use in which gas sensors are incorporated that an alarm concentration is set to 100 to several hundred ppm with respect to isobutane used as a fuel gas. With gas leak alarm units for household use, an alarm concentration is often set to several thousand ppm (e.g. 4000 ppm) with respect to methane used as a fuel gas. Table 2 shows concentrations of hydrogen and alcohol which are examples of miscellaneous gases which result in the same sensor output as 100 ppm isobutane. Table 3 shows concentrations of hydrogen and alcohol which are examples of miscellaneous gases which result in the same sensor output as 4000 ppm methane.

It will be seen from Table 2 that the gas sensors having platinum (Pt), palladium (Pd), rhodium (Rh) and gold (Au) electrodeposited on the platinum electrode have sufficient selectivity for isobutane as opposed to miscellaneous gases.

It will be seen from Table 3 that the gas sensors having platinum (Pt), palladium (Pd), silver (Ag), rhodium (Rh) silcon dioxide (SiD$_2$) and copper (Cu) electrodeposited on the platinum electrode have sufficient selectivity for methane as opposed to miscellaneous gases.

Where palladium was additionally electrodeposited on the platinum electrode on which platinum had been electrodeposited, data was obtained similar to those of platinum or palladium alone being electrodeposited in Tables 2 and 3.

This proves that where two or more

TABLE 2

Concentrations of $H_2$ and $C_2H_5OH$ Vapor
Corresponding to Alarm Concentration
100 ppm of Isobutane

| misc. gases | substances deposited on Pt electrode | | | | | | |
|---|---|---|---|---|---|---|---|
| (vol %) | none | Pt | Pd | Au | Ag | Rh | Cu | SiO$_2$ |
| $H_2$ | 0.02 | 0.16 | 0.14 | 0.11 | 0.05 | 0.12 | 0.05 | 0.06 |
| $C_2H_5OH$ | 0.07 | 0.26 | 0.20 | 0.12 | 0.11 | 0.1 | 0.10 | 0.15 |

TABLE 3

Concentrations of $H_2$ and $C_2H_5OH$ Vapor
Corresponding to Alarm Concentration
4000 ppm of Methane

| misc. gases | substances deposited on Pt electrode | | | | | | |
|---|---|---|---|---|---|---|---|
| (vol %) | none | Pt | Pd | Au | Ag | Rh | Cu | SiO$_2$ |
| $H_2$ | 0.15 | >1.0 | >1.0 | 0.15 | 0.40 | 0.30 | >1.0 | 0.45 |
| $C_2H_5OH$ | 0.30 | >0.4 | >0.4 | >0.4 | >0.4 | >0.4 | >0.4 | >0.4 | of the above substances are electrodeposited on the same electrode, an effect is produced which is similar to the case of each substance being electrodeposited.

The conditions for electrodepositing platinum, palladium, gold, rhodium, copper and silver, and for chemical vapor deposition of silicon dioxide are listed below.

Platinum: Platinum was electrodeposited on the platinum electrode in an aqueous solution of $H_2PtCl_6$ in 0.01 mol/l with an electrolytic voltage of 2.0 V for 90 seconds.

Palladium: Palladium was electrodeposited on the platinum electrode in an aqueous solution of $PdCl_2$ in 0.01 mol/l with an electrolytic voltage of 2.0 V for 60 seconds.

Gold: Gold was electrodeposited on the platinum electrode in an aqueous solution of $HAuCl_4$ in 0.01 mol/l with an electrolytic voltage of 2.0 V for 60 seconds.

Rhodium: Rhodium was electrodeposited on the platinum electrode in an aqueous solution of $RhCl_3$ in 0.01 mol/l with an electrolytic voltage of 2.0 V for 60 seconds.

Copper: Copper was electrodeposited on the platinum electrode in an aqueous solution of $CuSO_4$ in 0.01 mol/l with an electrolytic voltage of 2.0 V for 90 seconds.

Silver: Silver was electrodeposited on the platinum electrode in an aqueous solution of $AgNO_3$ in 0.01 mol/l with an electrolytic voltage of 2.0 V for 90 seconds.

Silicon dioxide: Silicon dioxide was deposited on the platinum electrode by chemical vapor deposition, heating the platinum electrode to about 500° C. for about 60 minutes in an atmosphere of saturated vapor concentration at room temperature (e.g. 4.2 vol % at 20° C.) of hexamethyl di-siloxane {$(CH_3)_3OSiO(CH_3)_3)$}.
(Experiment 3)

In the preceding experiments, investigations were made of variations in the sensitivity of gas sensors having metals and the like deposited on the platinum electrode formed of a platinum wire.

In Experiment 3, gas sensors having an electrode formed by electrodepositing platinum on a wire of platinum-rhodium alloy (20 um$\phi$) (hereinafter referred to as Pt-Rh), i.e. a precious metal wire other than the platinum wire were manufactured, and the sensitivity of these sensors to various gases were measured. These gas sensors have a similar construction to the gas sensors in Experiment 1 (see FIG. 1).

Platinum was electrodeposited on the Pt-Rh wire in an aqueous solution of $H_2PtCl_6$ in 0.01 mol/l with an electrolytic voltage of 2.0 V for 90 seconds.

Figure 7A:
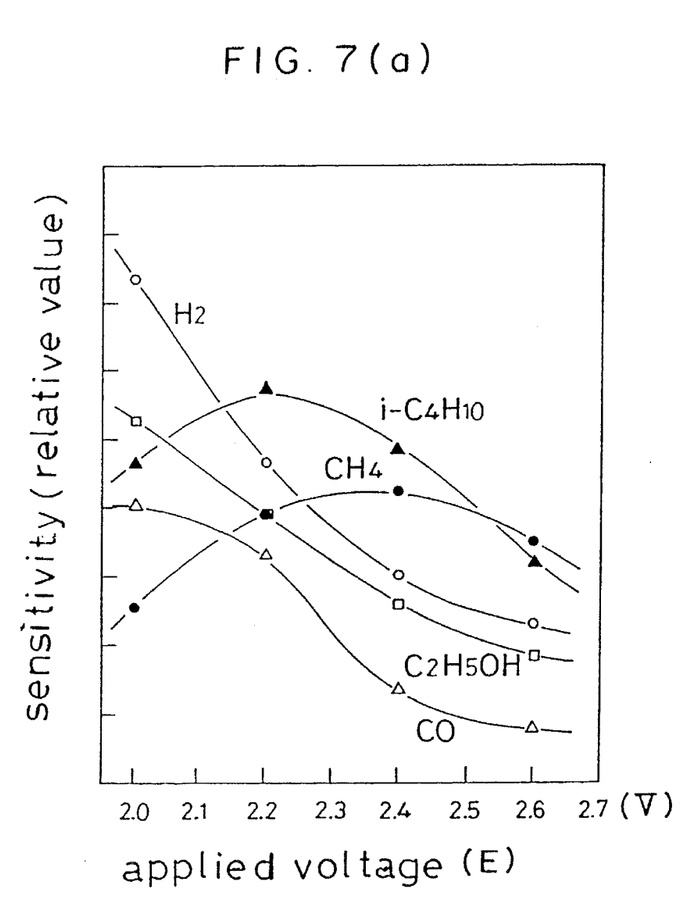
FIG. 7(a) is a graph showing applied voltage dependence of sensitivity of a comparative example gas sensor C using a Pt-Rh wire electrode to various gases having a concentration of 1000 ppm.
Figure 7B:
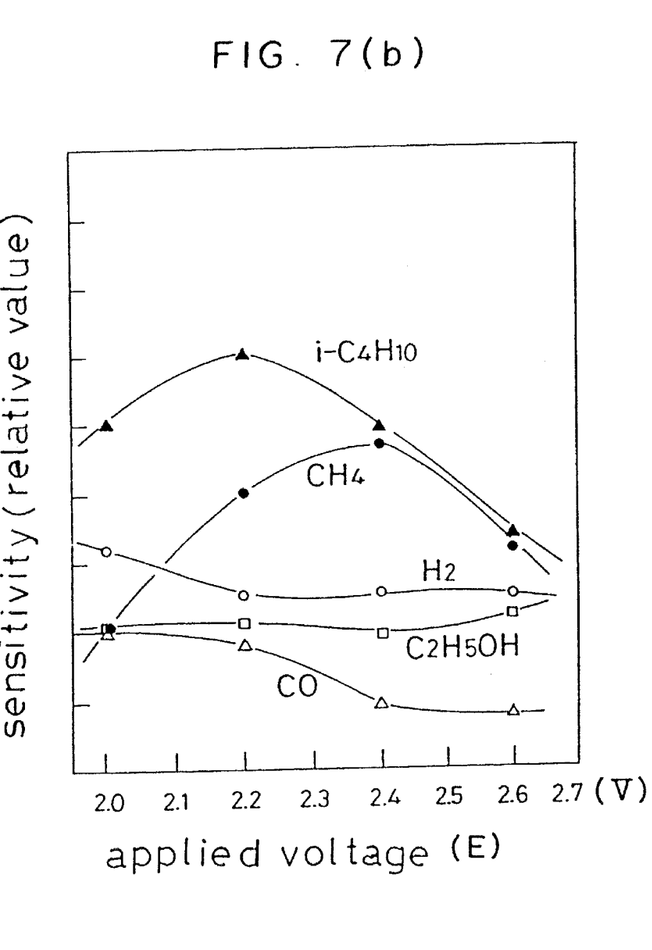
FIG. 7(b) is a graph showing applied voltage dependence of a gas sensor D of the present invention using a Pt-Rh wire electrode carrying platinum electrodeposited thereon to various gases having a concentration of 1000 ppm.

FIG. 7(a) shows applied voltage dependence of the sensitivity V to various gases in a concentration of 1000 ppm of a comparative example gas sensor C employing an untreated Pt-Rh wire having no electrodeposit of platinum. FIG. 7(b) shows applied voltage dependence of the sensitivity ΔV to various gases in a concentration of 1000 ppm of a gas sensor D of the present invention employing the Pt-Rh wire having an electrodeposit of platinum. A comparison of FIGS. (b) and (a) shows that, with the electrodeposition of platinum, the sensor outputs with respect to miscellaneous gases such as hydrogen, alcohol and carbon monoxide are far below the sensor outputs with respect to methane and isobutane. Thus, the gas sensor D of the present invention may be given excellent fuel gas selectivity with respect to miscellaneous gases.

The applied voltage dependence of the sensitivity Lo hydrogen and alcohol is also slight in a range of voltage application from 2.2 to 2.6 V. Thus, as does the gas sensor B in Experiment 1, this gas sensor D has desirable characteristics for use in town gas alarm units for household use.

As in Experiment 2, Table 4 shows concentrations of hydrogen and alcohol which are examples of miscellaneous gases which result in the same sensor output as 100 ppm isobutane. Table 5 shows concentrations of hydrogen and alcohol which are examples of miscellaneous gases which result in the same sensor output as 4000 ppm methane.

It will be seen from Table 4 that the gas sensors having platinum electrodeposited on the Pt-Rh wire electrode have the selectivity for isobutane as opposed to miscellaneous gases about twice that of the gas sensors having no electrodeposit of platinum.

It will be seen from Table 5 also that the gas sensors having platinum electrodeposited on the Pt-Rh wire electrode have the selectivity for isobutane as opposed to miscellaneous gases about twice that of the gas sensors having no electrodeposit of platinum.

The Pt-Rh wire has a smaller resistance temperature coefficient and greater mechanical strength than platinum, and is preferred to platinum as an electrode material.
(Experiment 4)

In this experiment, thermal decomposition was used instead of the foregoing electrodeposition as a

TABLE 4

Concentrations of $H_2$ and $C_2H_5OH$ Vapor
Corresponding to Alarm Concentration
100 ppm of Isobutane

| misc. gases (vol %) | Pt-Rh wire | platinum on Pt-Rh wire |
|---|---|---|
| $H_2$ | 0.04 | 0.08 |
| $C_2H_5OH$ | 0.05 | 0.10 |

TABLE 5

Concentrations of $H_2$ and $C_2H_5OH$ Vapor
Corresponding to Alarm Concentration
4000 ppm of Methane

| misc. gases (vol %) | Pt-Rh wire | platinum on Pt-Rh wire |
|---|---|---|
| $H_2$ | 0.04 | 0.08 |

TABLE 5-continued

Concentrations of $H_2$ and $C_2H_5OH$ Vapor
Corresponding to Alarm Concentration
4000 ppm of Methane

| misc. gases (vol %) | Pt-Rh wire | platinum on Pt-Rh wire |
|---|---|---|
| $C_2H_5OH$ | 0.05 | 0.10 | method of causing a metal to adhere to a precious metal electrode. This method is carried out by dropping a solution (aqueous solution or nonaqueous solution) of a metallic salt in a selected concentration to a heated electrode. The resulting thermal decomposition causes the metal or metallic oxide to adhere to the electrode. However, this method is applicable only to the type of metals whose precursors, i.e. metallic salts (complex salts), are in a state of solution.

In this experiment, attempts were made for adhesion by thermal decomposition to a platinum electrode surface of platinum (Pt), palladium (Pd), gold (Au), silver (Ag), rhodium (Rh) and iridium (Ir). Aqueous solutions of $H_2PtCl_6$, $PdCl_2$, $HAuCl_4$, $AgNO_3$, $RhCl_3$ and $IrCl_3$ in 0.01 mol/l, respectively, were used as metallic salts.

Briefly, the thermal decomposition process was carried out in the following steps:

(1) The electrode was heated at 600° C., and the aqueous solution of each metallic salt was dropped on the electrode.

(2) Water evaporated, and the metallic salt formed into microcrystals on the electrode.

(3) The electrode was kept heated at 600° C., whereby the microcrystalline deposit was decomposed and adhered to the electrode surface.

As in Experiment 1, gas sensors were manufactured by forming a layer of tin oxide semiconductor on the electrodes thus obtained. The sensitivity of each gas sensor to various gases was measured as in Experiment 2. Table 6 shows concentrations of hydrogen and alcohol which are examples of miscellaneous gases which result in the same sensor output as 100 ppm isobutane. Table 7 shows concentrations of hydrogen and alcohol which are examples of miscellaneous gases which result in the same sensor output as 4000 ppm methane.

It will be seen from Table 6 that the gas sensors having platinum, palladium and gold deposited on the platinum electrode by thermal decomposition have sufficient selectivity for isobutane as opposed to miscellaneous gases.

It will be seen from Table 7 that the gas sensors having platinum, palladium, gold, silver and rhodium deposited on the platinum electrode by thermal decomposition have sufficient selectivity for methane as opposed to miscellaneous gases.

(Summary of Experiments 1 to 4)
Experiments 1 to 4 described hereinbefore may be

TABLE 6

Concentrations of $H_2$ and $C_2H_5OH$ Vapors
Corresponding to Alarm Concentration
100 ppm of Isobutane

| misc. gases | substances deposited on Pt electrode by t. decom. | | | | | | |
|---|---|---|---|---|---|---|---|
| (vol %) | none | Pt | Pd | Au | Ag | Rh | Ir |
| $H_2$ | 0.02 | 0.15 | 0.10 | 0.10 | 0.03 | 0.10 | 0.006 |
| $C_2H_5OH$ | 0.07 | 0.23 | 0.15 | 0.11 | 0.009 | 0.015 | 0.006 |

TABLE 7

Concentrations of $H_2$ and $C_2H_5OH$ Vapors
Corresponding to Alarm Concentration
4000 ppm of Methane

| misc. gases | substances deposited on Pt electrode by t. decom. | | | | | | |
|---|---|---|---|---|---|---|---|
| (vol %) | none | Pt | Pd | Au | Ag | Rh | Ir |
| $H_2$ | 0.15 | 0.70 | 0.60 | 0.70 | 0.40 | 0.40 | 0.10 |
| $C_2H_5OH$ | 0.30 | >0.4 | >0.4 | >0.4 | >0.4 | >0.4 | 0.15 | summarized as follows:

1. Gas sensitivity characteristics of a semiconductor type gas sensor may be controlled by depositing a metal or the like of the same type or a different type such as by electrodeposition on an electrode surface at the interface between a tin oxide semiconductor and an electrode to form a high surface potential.

2. Gas sensitivity characteristics of a gas sensor may be adjusted by selecting a type of substance deposited on the electrode surface, thereby selectively reducing the sensitivity to miscellaneous gases such as hydrogen and alcohol that interfere with detection of fuel gases such as methane and isobutane.

In the foregoing experiments according to the present invention, the gas sensors include an electrode formed of a single coiled wire acting also as a heater as shown in FIG. 1. The gas sensors may include two wires may be used instead, one of which acts as the electrode and the other as the heater.

Figure 8:
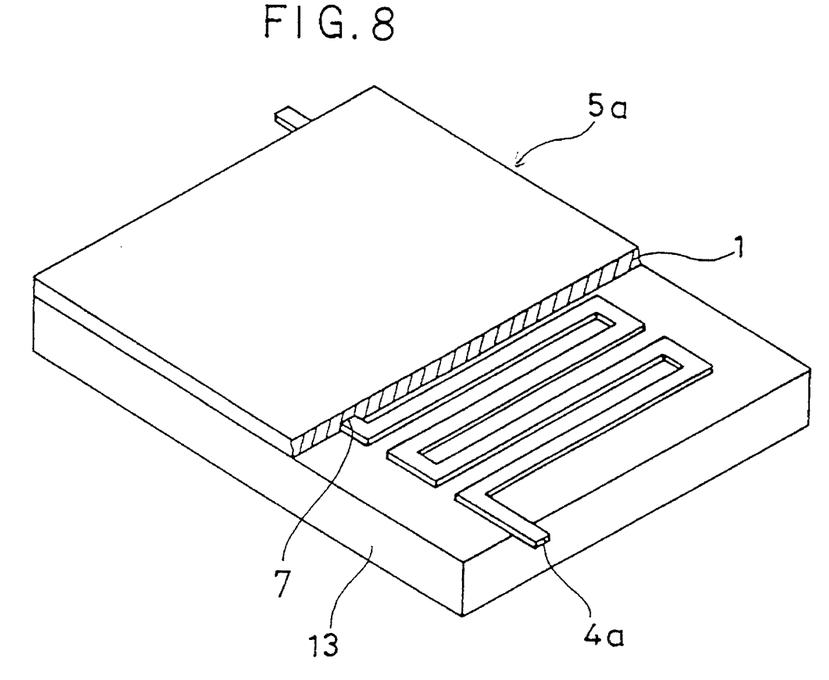
FIG. 8 is a perspective view, partly in section, of a substrate type, semiconductor type gas sensor in another embodiment of the present invention.
Figure 9:
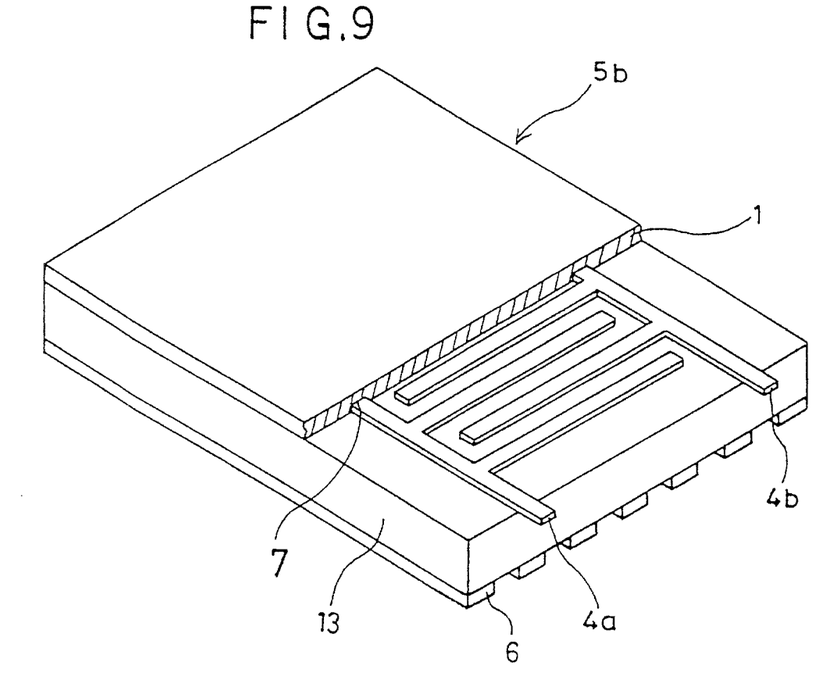
FIG. 9 is a perspective view, partly in section, of a substrate type, semiconductor type gas sensor in a further embodiment of the present invention.

(Experiments 5 and 6)
In Experiments 5 and 6, substrate type, semiconductor type gas sensors were manufactured as shown in FIGS. 8 and 9, which comprised a heat resisting and electrically insulating substrate such as of glass, silica, silicon or sapphire, and electrodes formed on the substrate. Experiments similar to Experiment 1 were carried out on these gas sensors.

Specifically, platinum electrode 4a or electrodes 4a and 4b were formed by vacuum deposition or printed on an alumina substrate 13. Then, a barrier layer 7 was formed by electrodepositing platinum on the platinum electrode 4a or electrodes 4a and 4b which were thereafter covered with a layer 1 of tin oxide semiconductor as in Experiment 1. No alumina is electrodeposited on the alumina substrate 13 since no voltage is applied to the latter. The substrate type, semiconductor type gas sensor 5b shown in FIG. 9 has a separate heater 6 formed on a back surface of the alumina substrate 13.

Measurement was made of applied voltage dependence of the sensitivity of the gas sensor 5a and temperature dependence of the sensitivity of the gas sensor 5b to various gases such as methane, isobutane and hydrogen. As a result, data similar to those of Experiment 1 shown in FIG. 6(b) were obtained.

To summarize Experiments 1 to 6, where gas sensors are constructed to have a higher surface potential than a surface potential naturally formed between a metallic oxide semiconductor and a precious metal electrode, gas sensitivity characteristics of the sensors may be controlled by forming a barrier layer on the electrode surface by electrodeposition, thermal decomposition, chemical vapor deposition, vacuum deposition, ion plating, ion spattering, or ion injection.

Such a barrier layer need not be formed uniformly over the entire surface of the precious metal electrode, but may be formed partially, intermittently or sporadically on the electrode surface. In short, it will serve the purpose if the electrode surface has decreased active points and increased inactive points.

The layer of metallic oxide semiconductor may include any of various substances as a main component, apart from tin oxide, such as zinc oxide or indium oxide. The electrode may comprise, in addition to platinum, Pt-Rh, ruthenium and iridium, gold and other precious metals, substances in the Groups VIII and IB, in the periodic table of elements or alloys thereof that have, for example, excellent heat resistance and anticorrosive property.

What is claimed is:

1. A gas sensor for use in a leak detector for detecting a fuel gas such as town gas, the sensor comprising:

a precious metal electrode; and a semiconductor layer at least partly covering said precious metal electrode, wherein:

said semiconductor layer includes, as a main component, at least one substance selected from the group consisting of tin oxide, zinc oxide and indium oxide;

said precious metal electrode is formed of a substance selected from the group consisting of platinum, gold, ruthenium, lead, silver, iridium, and alloys thereof;

a barrier layer having a high potential is formed between said precious metal electrode and said semiconductor layer and on a surface of said precious metal electrode; and said barrier layer comprises either a substance formed by electrodeposition and selected from the group consisting of platinum, palladium, gold and rhodium, or a substance formed by thermal decomposition and selected from the group consisting of platinum, palladium and gold, said barrier layer being capable of enhancing sensitivity to isobutane gas relative to other gases.

2. A gas sensor as claimed in claim 1, wherein said semiconductor layer has tin oxide as the main component thereof, and said barrier layer is formed of platinum.

3. A gas sensor for use in a leak detector for detecting a fuel gas such as town gas, the sensor comprising:

a precious metal electrode; and a semiconductor layer at least partly covering said precious metal electrode, wherein:

said semiconductor layer includes, as a main component, at least one substance selected from the group consisting of tin oxide, zinc oxide and indium oxide;

said precious metal electrode is formed of a substance selected from the group consisting of platinum, gold, ruthenium, lead, silver, iridium, and alloys thereof;

a barrier layer having a high potential is formed between said precious metal electrode and said semiconductor layer and on a surface of said precious metal electrode; and said barrier layer comprises either a substance formed by electrodeposition and selected from the group consisting of platinum, palladium, rhodium, silver and copper or silicon oxide formed by chemical deposition or a substance formed by thermal decomposition and selected from the group consisting of platinum, palladium, gold, rhodium and silver said barrier layer being capable of enhancing sensitivity to methane gas relative to other gases.

4. A gas sensor as claimed in claim 3, wherein said semiconductor layer includes tin oxide as the main component and said barrier layer comprises platinum.

5. A gas sensor as claimed in claim 3, wherein said barrier layers comprises silicon oxide.

6. A gas sensor for use in a leak detector for detecting a fuel gas such as town gas, the sensor comprising:

a substrate;

a precious metal electrode formed on said substrate; and a semiconductor layer at least partly covering said precious metal electrode; wherein:

said semiconductor layer includes, as a main component, at least one substance selected from the group consisting of tin oxide, zinc oxide and indium oxide;

said precious metal electrode is formed of a substance selected from the group consisting of platinum, gold, ruthenium, lead, silver, iridium, and alloys thereof;

a barrier layer having a high potential is formed between said precious metal electrode and said semiconductor layer and on a surface of said precious metal electrode; and said barrier layer comprises either a substance formed by electrodeposition and selected from the group consisting of platinum, palladium, gold and rhodium, or a substance formed by thermal decomposition and selected from the group consisting of platinum, palladium and gold, said barrier layer being capable of enhancing sensitivity to isobutane gas relative to other gases.

7. A gas sensor as claimed in claim 6, wherein said semiconductor layer has tin oxide as the main component thereof, and said barrier layer is formed of platinum.

8. A gas sensor as claimed in claim 6, wherein said substrate is formed of a substance selected from the group consisting of alumina, glass, silica, silicon and sapphire.

9. A gas sensor as claimed in claim 8, wherein said substrate is formed of alumina and includes a heater mounted on a back surface thereof.

10. A gas sensor for use in a leak detector for detecting a fuel gas such as town gas, the sensor comprising:

a substrate;

a precious metal electrode formed on said substrate; and a semiconductor layer at least partly covering said precious metal electrode, wherein:

said semiconductor layer includes, as a main component, at least one substance selected from the group consisting of tin oxide, zinc oxide and indium oxide;

said precious metal electrode is formed of a substance selected from the group consisting of platinum, gold, ruthenium, lead, silver, iridium, and alloys thereof;

a barrier layer having a high potential is formed between said precious metal electrode and said semiconductor layer and on a surface of said precious metal electrode; and said barrier layer comprises either a substance formed by electrodeposition and selected from the group consisting of platinum, palladium, rhodium, silver and copper or silicon oxide formed by chemical deposition or a substance formed by thermal decomposition and selected from the group consisting of platinum, palladium, gold, rhodium and silver said barrier layer being capable of enhancing sensitivity to methane gas relative to other gases.

11. A gas sensor as claimed in claim 10, wherein said semiconductor layer includes tin oxide as the main component and said barrier layer comprises platinum.

12. A gas sensor as claimed in claim 10, wherein said barrier layers comprises silicon oxide.

13. A gas sensor as claimed in claim 10, wherein said substrate is formed of a substance selected from the group consisting of alumina, silica, silicon and sapphire.

14. A gas sensor as claimed in claim 13, wherein said substrate is formed of alumina and includes a heater mounted on a back surface thereof.

* * * * *